United States Patent [19]

Hignett

[11] 4,385,008
[45] May 24, 1983

[54] BLEACHING AGENT

[75] Inventor: Geoffrey J. Hignett, Statham, England

[73] Assignee: Interox Chemicals Limited, London, England

[21] Appl. No.: 193,078

[22] Filed: Oct. 2, 1980

[30] Foreign Application Priority Data

Oct. 18, 1979 [GB] United Kingdom ............... 7936178
Dec. 22, 1979 [GB] United Kingdom ............... 7944312

[51] Int. Cl.$^3$ ........................................... C07C 179/16
[52] U.S. Cl. ............................. 260/502 R; 562/493; 562/492; 568/558; 568/566
[58] Field of Search ................. 260/502 R; 568/558, 568/566, 559; 252/186; 562/493, 492

[56] References Cited

U.S. PATENT DOCUMENTS

| | | | |
|---|---|---|---|
| 2,813,896 | 11/1957 | Krimm | 260/502 R |
| 2,839,470 | 6/1958 | Warren | 562/493 |
| 3,076,852 | 2/1963 | Lohringer et al. | 260/502 R |
| 3,232,979 | 2/1966 | Blumbergs | 260/502 R |
| 3,247,244 | 4/1966 | Blumbergs | 260/502 R |
| 3,494,787 | 2/1970 | Lund et al. | 260/502 R |
| 3,510,512 | 5/1970 | Jourdan-Laforte | 260/502 R |
| 3,639,285 | 2/1972 | Nielsen | 252/186 |
| 3,929,875 | 12/1975 | Rapko et al. | 252/186 |
| 4,060,535 | 11/1977 | Cinco | 562/493 |
| 4,134,850 | 1/1979 | McCrudden et al. | 562/493 |
| 4,154,695 | 5/1979 | McCrudden et al. | 562/566 |
| 4,178,300 | 12/1979 | van der Berg | 562/493 |
| 4,225,451 | 9/1980 | McCrudden et al. | 260/502 R |
| 4,259,201 | 3/1981 | Cockrell, Jr. et al. | 252/186 |
| 4,288,388 | 9/1981 | McCrudden et al. | 260/502 R |
| 4,294,717 | 10/1981 | Couderc et al. | 260/502 R |

FOREIGN PATENT DOCUMENTS

| | | | |
|---|---|---|---|
| 36619 | 10/1969 | Australia | 260/502 R |
| 2332322 | 5/1977 | France . | |
| 363329 | 9/1962 | Switzerland | 260/502 R |
| 1041983 | 9/1966 | United Kingdom | 260/502 R |
| 1112778 | 5/1968 | United Kingdom | 260/502 R |
| 1156240 | 6/1969 | United Kingdom | 260/502 R |

Primary Examiner—Werren B. Lone
Attorney, Agent, or Firm—Larson and Taylor

[57] ABSTRACT

The present invention relates to the provision in solid form of the magnesium salt of certain aromatic, cycloaliphatic or conjugated aliphatic compounds containing a peroxycarboxylic acid group and a carboxylate group, and optionally also an alkyl, carboxylate, sulphonate, nitro, chloro or bromo group, which can be employed as bleaching agents. One especially referred example is magnesium monoperoxyphthalate having the formula:

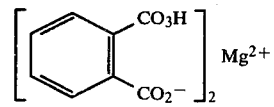

The invention also provides processes for the preparation of the salts, by reaction between a magnesium compound and the organic peroxyacid/carboxylate compound in a solvent from which the salt precipitates, the latter preferably being obtained by reaction between hydrogen peroxide and the corresponding anhydride under controlled reaction conditions of temperature and reagent ratios. The invention further provides desensitized compositions and washing compositions containing the bleaching agents and processes for washing or bleaching, employing them, preferably at from ambient to 60° C.

22 Claims, No Drawings

BLEACHING AGENT

The present invention relates to bleaching agents, processes for their preparation, bleaching compositions and washing compositions containing them and processes for bleaching and for washing employing the bleaching agent or compositions containing them.

For many years, many European washing compositions have contained an active oxygen-containing compound which have normally been an alkali metal persalt such as sodium perborate tetrahydrate or sodium percarbonate, in order to oxidise various of the stains during the course of washing household cloths and articles. Similarly in America, compositions containing an active oxygen-containing compound often in tablet form are available for addition to either the washing or rinsing stages of the washing process. At present, there is a trend towards washing at lower temperatures, i.e. at a temperature of ambient to 60° C. instead of the much higher temperatures of from 80° C. to boiling point that has been practised in Europe in order to obtain most benefit from the active oxygen content of the alkali metal persalts that have been conventionally employed hitherto. The trend results from the increasing use of synthetic fibres for the manufacture of clothing and other washable household articles and the use of special finishes for them, both of which can suffer if washing temperatures approaching boiling point are employed. Moreover, the increasing cost of energy means that it is increasingly desirable for economic reasons to be able to wash at low temperatures. In order to improve the washing performance of compositions at low washing temperatures, it has already been proposed to employ organic peroxyacids, including monoperoxyphthalic acid (which may be referred to herein as MPPA) which offers very acceptable washing performance but which has the disadvantage of relatively poor storage stability, both when stored in admixture with diluents and also with other components of household washing or detergent compositions. When we use the term 'storage stability' herein, it is in relation to the rate at which the peroxygen composition loses its active oxygen content during storage. We have also discovered that monoperoxyphthalic acid, although not a skin sensitiser itself, inevitably forms diphthaloyl peroxide during storage which in a recent and sensitive standard test has exhibited properties of skin sensitisation, thereby rendering monoperoxyphthalic acid less acceptable to manufacturers of washing or bleaching compositions, even though its bleaching properties appear otherwise to be acceptable.

It has been disclosed in British patent specification No 1 112 778 that a particulate peroxyphthalic acid can be intimately mixed with an alkali metal or alkaline earth metal salt which retains water of hydration at temperatures below 60° C. and in British Pat. No. 1 156 240 that peroxyphthalic acids can be encapsulated with such inorganic salts, but such methods do not markedly affect the rate of formation of diphthaloyl peroxide on storage and thus do not alleviate the second problem.

In British patent specification No. 1 041 983, alkali metal and ammonium salts of MPPA are prepared. The specification is silent on the practical problems of skin sensitisation and we have found that the storage stability of the alkali metal and ammonium salts of MPPA are worse than that of MPPA itself, so that therefore this patent does not suggest a way of ameliorating or overcoming the unacceptability of MPPA.

According to one aspect of the present invention, there is provided in solid form the magnesium salt of:

Class (1) an aromatic carbocyclic compound substituted around the aromatic nucleus by a carboxylate group and a peroxycarboxylic acid group both groups being derivable from the corresponding aromatic carbocyclic anhydride by reaction with hydrogen peroxide, said aromatic carboxylic compound optionally being further substituted by at least one of the groups selected from alkyl, carboxylate, sulphonate, nitro, chloro and bromo groups or Class (2) a cycloaliphatic compound substituted around the cycloaliphatic nucleus by a carboxylate group and a peroxycarboxylic acid group both groups being derivable from the corresponding cycloaliphatic carbocyclic anhydride by reaction with hydrogen peroxide, said cycloaliphatic carboxylic compound optionally being further substituted by at least one of the groups selected from alkyl, carboxylate, sulphonate, nitro, chloro and bromo groups or Class (3) compounds other than those in class 1 in which the carbonyl group of the peroxycarboxylic acid substituent is conjugated with the carbonyl group of a carboxylate substituent via olefinic unsaturation which carboxylate and peroxycarboxylic acid substituents are derivable from the corresponding anhydride by reaction with hydrogen peroxide.

In a second aspect of the present invention there is provided a process for the production of bleaching agents in classes 1, 2, or 3 comprising the step of reacting the corresponding compound containing a carboxylic acid group and a monoperoxy acid group with a magnesium compound in the presence of a solvent so selected that the resultant magnesium salt precipitates therefrom.

In a third aspect of the present invention there are provided bleaching compositions comprising one or more of the magnesium salts of classes 1, 2 or 3 as described hereinbefore in intimate mixture with a desensitising amount of one or more desensitising diluents.

By the term "desensitising diluent" herein, we mean a compound in solid form and which either does not contain any active oxygen or contains such a small proportion that it itself is not readily sensitive to impact or friction or thermal shock and a desensitising amount is such an amount that the composition is non-hazardous in the standard drop-weight test described hereinafter.

According to a fourth aspect of the present invention there are provided washing compositions containing a surfactant, a builder and a bleaching agent wherein the bleaching agent is one or more of the magnesium salts of classes 1, 2, or 3.

It will be recognised that where reference is made herein to the magnesium salt of a particular peroxycarboxylic acid compound, the salt is formed from the carboxylic acid group and not the peroxycarboxylic acid substituent so that the latter remains intact. Moreover, it will be recognised that where the carbocyclic nucleus is substituted additionally by a member of the group described with respect to class 1, the resultant product can in general be a mixture of isomers particularly when the product is obtained by hydrogen peroxide oxidation of the corresponding anhydride. Thus, for example, the product obtained by reacting hydrogen peroxide and magnesium oxide with trimellitic anhydride is a mixture containing, it is believed, benzene-1,3-dicarboxylate-4-peroxycarboxylic acid and benzene-1,4-dicarboxylate-3-peroxycarboxylic acid. It will be further recognised that the magnesium salt derived from trimellitic anhydride falls within class 1. Further examples within class 1 include the product obtained from pyromellitic anhydride by oxidation with hydrogen peroxide and neutralisation. Once again the product is believed to be a mixture of isomers comprising benzene-1,4-dicarboxylate-2,5-diperoxycarboxylic acid, and benzene-1,5-dicarboxylate-2,4-diperoxycarboxylic acid. Thus, the products derived from trimellitic and pyromellitic anhydrides are both salts in which the benzene nucleus is substituted by one or more further carboxylate groups. Desirably, in class 1 compounds, where the benzene nucleus is further substituted by a nitro, chloro or bromo substituent, the substituent is para to either the carboxylate substituent or the peroxycarboxylic acid substituent, and that in practice, where the product is obtained from the corresponding anhydride, a mixture of both isomers is likely to occur. It will be understood that in such reactions, the relative positions of the additional substituent and the carbonyl groups originally forming part of the anhydride group and later forming respectively the carboxylate and peroxycarboxylic acid substituents does not change and the two isomers arise merely as a result of the asymmetry of the molecule. Where the additional substituent in the benzene nucleus is an alkyl group, it can be a short chain alkyl, for example methyl, ethyl or propyl up to a long chain hydrophobic substituent such as dodecyl, hexadecyl, or octadecyl substituents. Conveniently, the alkyl substituent can be either ortho or para to either the carboxylate or the peroxycarboxylic acid substituents.

One especially suitable and convenient member of class 1 is magnesium monoperoxyphthalate, by which we mean herein the compound having the formula

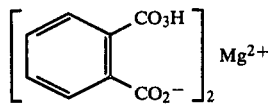

It will be recognised that the salt is that of the carboxylic acid group only and that the peroxy group remains in acid form. When the salt is prepared by the processes described herein, in the solid form, the resultant crystalline material is hydrated. Surprisingly, the aforementioned magnesium salt, which for the sake of brevity may be referred to herein alternatively as MMPP, demonstrates better storage stability than either MPPA itself, or the alkali metal or ammonium salts thereof, and in this respect MMPP typifies the relationship between the magnesium salt of compounds in classes 1 to 3 herein on the one hand and the corresponding alkali metal or ammonium salts and the monoperoxyacid on the other hand.

Some of the salts included in class 2 can be regarded as the aromatic compounds in class 1 which have been hydrogenated. Examples of compounds falling within class 2 include the magnesium salt of cyclohex-4-ene-1-carboxylate-2-peroxycarboxylic acid. Preferably, the compounds in class 2 are fully saturated as in the magnesium salt of cyclohexane-1-carboxylate-2-peroxycarboxylic acid, otherwise referred to as the magnesium salt of hexahydro-monoperoxyphthalate. Other compounds falling within class 2 include the analogues of hexahydro-monophthalate (magnesium salts) further substituted in, for example, the 3 or 4 position by a substituent such as alkyl, nitro, carboxylate or sulphonate group. Compounds falling within class 3, it will be recognised, include magnesium monoperoxy-maleate and corresponding compounds in which the olefinic group is further substituted by an alkyl group. The alkyl group when present in compounds in classes 2 or 3 can be methyl through to long chain such as octadecyl.

Although the production of the magnesium salts in classes 1 to 3 described hereinbefore is described hereinafter with reference specifically to the production of MMPP, the other salts can be made similarly by making the appropriate changes to, for example, starting materials and mole ratios as necessary, using the same general reaction routes, conditions and solvents, and in consequence, the description is to be understood to be representative of the manufacture of salts in classes 1 to 3. Thus, in the same way as for MMPP, the convenient starting point for many of the compounds described herein is the corresponding anhydride, and again as with MMPP preparation, the product contains non-peroxygenated product co-crystallised with the peroxygen species. The relative proportions of peroxygenated species and non-peroxygenated species obtained varies from compound to compound. Additionally, it will be recognised that where the compound contains one or more additional carboxylate groups, then the mole ratio of magnesium compound employed is increased over the ratio that would have been employed for MMPP production in order to allow for this, the preferred increase being proportionate to the increase in carboxylate groups present.

MPPA is produced conveniently by reaction between hydrogen peroxide and phthalic anhydride which can then be employed to produce MMPP by partial neutralisation with magnesium in the presence of a non-reactive organic solvent, the solvent and the relative amounts of the reagents and the solvent preferably being so selected that the liquid phase remains as a single phase and thus the liquid components do not separate to form an emulsion. By the term 'non-reactive' we mean that solvent does not react to any marked extent with hydrogen peroxide or the intermediate product (MPPA) or the final product (MMPP) under the prevailing reaction conditions i.e. during the period of time whilst the solvent remains in contact with a peroxy-compound. We have found that one suitable class of organic solvents comprises low molecular weight aliphatic esters. As a general guide, such esters can contain from 3 to 10 carbon atoms in total and are, preferably, acetates, especially ethyl acetate, or propionates or formates.

The hydrogen peroxide is employed in the form of an aqueous solution. We have found that the presence of an amount of water comparable with the amount of hydrogen peroxide results in formation, in reasonable yield, of product in the reaction mixture. Whilst, naturally, use of excess water leads to a particulate product having a lower active-oxygen content and thus a lower conversion of phthalic anhydride to MMPP, it has been found surprisingly that if insufficient water is present the yield of MMPP drops substantially.

Analysis of solid MMPP demonstrated that MMPP as formed under the process conditions described herein is hydrated, and thus the reaction mixture preferably contains sufficient water for all the MMPP that is formed to be hydrated and precipitated out of solution.

In general, we prefer to use hydrogen peroxide and water in amounts equivalent to a 40 to 60% w/w aqueous hydrogen peroxide, or in the form of a solution having a concentration in that range already, although some MMPP can be produced where the concentration is somewhat outside the preferred range, but desirably still within the range 30 to 75% w/w hydrogen peroxide. The amount of the aqueous hydrogen peroxide or water and aqueous hydrogen peroxide in total that is employed in practice is often from 50 to 100 g per litre of organic solvent and where it is desired to minimise the use of solvent, the total amount is preferably within 10% of the maximum permissible whilst retaining a single phase liquid system, and desirably the amounts of phthalic anhydride and magnesium compound to be used are determined in accordance therewith, also taking into account the following preferred features.

The stoichiometric mole ratio of hydrogen peroxide to phthalic anhydride is 1:1. It is desirable to employ at least the stoichiometric ratio and preferably only a slight excess, i.e. in the range 1.01:1 to 1.2:1, and particularly 1.05:1 to 1.12:1. Naturally, it is possible to employ mole ratios outside these ranges but still in the range 1:2 to 2:1, particularly where for example the reaction mixtures are to be recycled. It will be recognised that when the solid phthalic anhydride is introduced, part dissolves and part can remain in solid form, thereby creating a slurry, and therefore it is desirable to maintain stirring to promote good solid/liquid contact. A convenient amount of anhydride to add is often from 0.6 to 1.5 moles per 1000 g reaction mixture, which in the case of phthalic anhydride is about 96 g to about 125 g per 1000 g final reaction mixture.

The final magnesium compound is preferably present in an amount theoretically sufficient to neutralise the carboxylic acid in all the monoperoxyphthalic acid produced by reaction between the phthalic anhydride and hydrogen peroxide. In order to achieve this, it is desirable to employ a mole ratio of magnesium compound as Mg to phthalic anhydride (PA) of at least 1:2 and conveniently less than 1:1. In more preferred embodiments the Mg:PA mole ratio is in the range 1:2 to 1.2:2, and in many of the preferred embodiments is approximately half the hydrogen peroxide:PA mole ratio. Where the anhydride contains or generates x carboxylate groups per molecule then the ranges are multiplied by x for example, 1x2:2 to 1.2x2:2. It is highly desirable to employ as the magnesium compound, one that does not introduce anions of strong acids. Compounds that fulfill that desideratum include magnesium oxide, magnesium hydroxide, magnesium carbonate and basic magnesium carbonates.

The order of introduction of the reagents into the solution can be varied. Thus, the aqueous hydrogen peroxide can be introduced into a slurry of magnesium compound and phthalic anhydride in the organic solvent or the introduction of the solid reagents can be first. Alternatively all three could be introduced together. However, it is important in any order of introduction to control the temperature during the period that the phthalic anhydride and hydrogen peroxide are brought into contact, herein termed the initial reaction period. By so doing, the proportion of monoperoxyphthalic acid reacting with further phthalic anhydride to form diphthaloyl peroxide can be minimised, and, where the temperature is in the region of 10° C. to 12° C. or lower during the initial reaction period, that proportion is substantially nil. It will be recognised that the maximum temperature appertaining throughout the initial reaction period that can be tolerated depends upon the proportion of diphthaloyl peroxide that can be tolerated, the higher the temperature the higher the proportion. For example, if the temperature is maintained at 20° C. during the initial reaction period, the proportion of diphthaloyl peroxide can be in the region of about 5%. In consequence, the reaction temperature during the initial reaction period is in practice in the range of 0° to 30° C. and preferably from 5° to 15° C.

After the reactants have been brought into contact or within 15 minutes thereof, the temperaure of the slurry can be allowed to rise, since the risk of diphthaloyl peroxide forming is much lower than during the initial reaction period, suitably to a temperature in the range of 15° to 30° C. During this latter period, MMPP is forming as a particulate solid. For a batch process, the secondary reaction period typically lasts from 0.5 hours to 5 hours, and often from 1 to 2 hours.

After the MMPP has been formed as a particulate precipitate, it can then be separated employing standard solid/liquid separators such as drum and plate filters, or centrifuges. It is then, preferably, washed with a non-aqueous solvent for phthalic anhydride, which can be, conveniently, a small amount of fresh solvent employed as the reaction solvent. The separated solid can then be dried, but preferably, where it is known that in the dried state it would not be sufficiently insensitive to impact or to thermal shock, it is desensitised whilst it is still in the damp state by intimate contact with a suitable amount of one or more of the desensitising compounds described herein.

Where separated liquor still contains hydrogen peroxide and/or phthalic anhydride and/or MPPA, it can be re-employed, suitably by making-up the concentrations of the reactants to within the ranges of mole ratios described hereinbefore and particularly to achieve steady-state levels under the reaction conditions described. Thus, the process in some embodiments, is cyclical comprising the steps of (i) dissolution of aqueous hydrogen peroxide, in a selected organic solvent and introduction of phthalic anhydride and magnesium compound therein, in amounts as described herein;
(ii) separating particulate MMPP from the liquid phase;
(iii) determining the contents of phthalic anhydride, MPPA, water, hydrogen peroxide and magnesium compound in the liquid phase;
(iv) recycling the liquid phase to step (i) for make-up of the reagents, preferably achieve steady state to levels, the process applying mutatis mutandis to the production of the other magnesium salts in classes 1 to 3. By so recycling, it has been found that the average particle size of the product can be increased, the proportion of fine particles in the product tending to diminish.

When a steady state is obtained step (iii) need not be carried out every cycle, but the previously calculated amounts used.

It will be recognised that the ratios of reagents introduced in subsequent cycles can appear to be outside the ranges of ratios specified earlier herein. Assuming that the volume of filtrate/washings on recycle is adjusted where necessary to approximately the same level the amount of phthalic anhydride introduced in subsequent cycles is, in many cases, approximately half that introduced in the first cycle, the amount of hydrogen peroxide introduced is approximately 60% of that introduced in the first cycle and the amount of magnesium oxide introduced likewise is substantially the same in first and subsequent cycles. In practice, this means that in the subsequent cycles the mole ratio of Mg:PA introduced is preferably in the range of 5:4 to 4:5, the hydrogen peroxide:PA mole ratio is preferably in the range of 1.1:1 to 1.3:1, and the amount of PA introduced is often in the range 0.35 to 0.75 moles per 1000 g reaction mixture.

The magnesium salts in classes 1 to 3, which, alternatively, may be referred to as MPX for brevity, of which one member is MMPP, can be desensitised by intimately contacting it, with a desensitising diluent, suitable methods including coating and admixture of particulate substances. Generally, the desensitised MPX composition consists of 20 to 70% w/w MPX preferably 40 to 60% w/w MPX (calculated as the anhydrous salt) and the balance being desensitising diluent, although, an MPX content of below 20% w/w could be employed particularly if one or more of the diluents perform a further useful function such as detergent builder. In practice, it will be recognised that MMPP as often prepared in processes described herein is much safer than many organic peroxides or peracids proposed hitherto for incorporation in detergent compositions, and in many cases passes the drop-weight test without any further diluent being employed, but naturally further diluent can still be employed, if desired, particularly where it can perform some additional function.

In the standard drop weight test by which impact sensitivity is measured, the apparatus comprises an anvil upon which the test sample is placed, and a weight located vertically above the anvil over the range of heights. In operation, 30 mg of the test sample which has been sieved to a particle size of below 710 microns is placed on the anvil, which is then centred and the sample tamped lightly under an impact of 5 Kg-cm. The weight is then dropped from a predetermined height and its effect observed. The test is then repeated at the same height, each time dropping the weight onto a fresh sample, and the proportion of positive results which occurred is then calculated. In broad terms, a positive result is said to occur when there is a significant change in the test sample, ranging at the one extreme from merely a discoloured sample, through an intermediate position of emission of a cloud of smoke, to the other extreme of an explosion. The figure that is usually quoted in the presentation of the results of this test is the median point $E_{50}$, which is the point at which 50% of the results at a given force are positive. In order to minimise any risks involved in performing this test, the tests are first carried out employing a very low force, a force well below the median point that the operator expects from experience, and the force is then progressively increased in subsequent series of tests until the median point $E_{50}$ is reached. Compositions having a median point $E_{50}$ of at least 200 Kg-cm are conventionally considered to be non-hazardous, but in order to provide a greater margin of safety, it is preferable to employ sufficient diluent that the composition has a median point of at least 300 Kg-cm.

A particularly important class of desensitising diluents employed in intimate particulate mixture with MPX or as a coating for MPX comprises alkali metal or alkaline earth metal salts of halogen-free acids having a first dissociation constant of at least $1 \times 10^{-3}$. Particularly, the alkali metal selected is either sodium or potassium, and of the alkaline earth metals, magnesium. Conveniently, the inert salt can be a sulphate or bisulphate, nitrate, ortho, pyro or polyphosphate. Especially preferred diluent salts include sodium sulphate, magnesium sulphate and sodium tripolyphosphate. It is especially desirable to employ a high proportion of the diluent salt in a dehydrated or lower hydrated form such as for example the lower hydrate of magnesium sulphate, so that free water can be removed from the bleaching composition during storage.

Such salts have the advantage of not only ameliorating the impact sensitivity of the organic peroxygen compound but also can improve the storage stability of MPX especially when MPX is intended for incorporation in particulate surfactant-containing washing compositions. Other inorganic salts that can be employed, if desired, include alkali metal or alkaline earth metal borates, including sodium metaborate, aluminium sulphate and aluminosilicates and clays particularly those which can readily absorb and retain water. Useable zeolites include the sodium forms of X, A, and Y and mixtures of two or more thereof. The sodium form of zeolite X and mixtures containing it and A or Y are especially suitable in that they are particularly efficient in removing magnesium from washing solutions in comparision with zeolites A and Y. Other inorganic diluent salts which can be employed include sodium perborate monohydrate or tetrahydrate which have the advantage of themselves providing some active oxygen for use in bleaching or washing, especially if elevated washing or bleaching temperatures are employed.

The diluent can also be selected from organic compounts that do not react with MPX and also are solid at 30° C. where the diluent comes into direct contact with MPX. Where the diluent does not come into direct contact with MPX, for example, where it is present as a second or outer coating, less unreactive classes of organic compounds can be employed too, in many cases to provide also some additional function such as to further protect MPX from adetergent environment during storage. Examples of unreactive organic diluents include hydrocarbon waxes, fatty acids, aromatic acids and aliphatic esters thereof, starch, cellulose and proteins. Examples of less unreactive compounds tend to contain one or more of hydroxyl, ether and amide groups.

Of the unreactive diluents, one very useful class comprises the hydrocarbon aliphatic or aromatic microcrystalline waxes, for example those obtained from distillation of crude oils, or polymers such as polyethylene or polypropylene, preferably having melting points in the range of 30° C. to 60° C. In order to improve their dispersion in use, the hydrocarbons can contain a dispersant e.g. 1% to 10% based on the weight of hydrocarbon, of a sulphonated surfactant in which any free acid has been neutralised.

Herein, fatty in the context of fatty acids, amides, alcohols etc indicates an alkyl chain of at least 9 carbon atoms length attached to the carboxyl, amide, methylol etc group. Although any aliphatic fatty acid can be used, for practical purposes, the acid normally contains from 10 to 26 carbon atoms, especially stearic acid, myristic acid and palmitic acid. Preferably the aliphatic acid has a melting point of about 40° C. e.g. lauric acid, so that it can be conveniently melted and used thereby to coat or bind together particles of MPX. Commercially available mixtures of fatty acids such as coconut fatty acids which contain a high proportion of lauric acid may conveniently be employed.

The diluent can be a dibasic aromatic acid, such as phthalic, isophthalic or terephthalic acid. Other suitable aromatic acids include benzoic acid, toluic acid and mellitic acid. If desired alkali or alkaline earth metal salts of the aromatic acids can be used including magnesium phthalate. The esters are preferably short chain aliphatic e.g. n-butyl iso-butyl or tertiary butyl, hexyl or pentyl esters, or aromatic, e.g. benzoyl or phenyl. Examples include n-butyl phthalate, and di-n-butyl phthalate.

Included within the term cellulosic materials are cellulose itself, and derivatives of it such as carboxymethylcellulose and methyl- or hydroxymethyl- cellulose. Included within the terms protein and starch materials are dextrin, gelatin and starch itself.

The class of less unreactive diluents includes aliphatic fatty acid alkanolamides, fatty alcohol polyglycol ethers, alkaryl polyglycol ethers, ethylene oxide/propylene oxide polymers, polyethylene glycol and fatty acid esters and amides thereof and glycerol and sorbitol esters and amides. Such compounds tend to include a high proportion of hydroxyl, ether or ester groups. Preferably they are separated from MPX by a layer of unreactive diluent. Within the class of such compounds, those melting at 60° C. or higher are preferred. In the cases of (a) esters derived from polyethylene glycol and fatty acid, (b) fatty acid alkanol amides, and (c) esters and amides derived from fatty acid and glycerol, the fatty acids from which they are derived preferably contain between 12 to 26 carbon atoms and can conveniently be lauric, myristic, palmitic or stearic or mixtures obtained commercially from natural sources, such as tallow fatty acids and coconut fatty acids. Desirably, the polyethylene glycol moiety contained in a diluent has a molecular weight of from 250 to 2000, preferably from 300 to 1200. Desirably, the alkanolamide moiety is short chain (such as $C_2$ to $C_6$) aliphatic alcohol moiety. In practice, the less unreactive diluent or diluents are used to a total amount of normally 0 to 20%, based on the diluted composition.

It will be recognised that appropriate techniques for bringing an inorganic or organic percompound into intimate contact with a diluent or increasing the particle size of such compounds are in themselves well known to skilled artisans in the field of peroxygen compound preparation, such techniques including granulation, e.g. in a pan-ball granulator, possibly using water or an organic solvent such as alcohol which is subsequently dried off in order to assist the granulation process, pelletisation or the formation of noodles, and such techniques can be employed in respect of MPX compounds. Similarly, techniques for coating percompounds with diluents by for example contacting particles of the former with the latter in a slurry or solution and removing the solvent, or in the molten state and cooling, using for example a fluidised bed, a rotating pan or disk or a spheroniser are also well known in themselves, and can similarly be applied to MPX compounds.

Washing compositions according to fourth aspect of the present invention preferably contain up to 40% by weight MPX, and usually at least 1% MPX. The amount of MPX incorporated would often be calculated in the light of the recommended concentration of washing composition to be used in the washing solution so as to provide available oxygen (Avox) concentrations described hereinafter, and taking into account the proportions of the surfactants and builders in the washing composition. Often, the concentration of MPX will be selected within the range of 2% to 20% and in many compositions is at least 5%, %s being by weight. It will, of course, be understood that the actual amount of bleaching agent to be included varies naturally with the amount of available oxygen in any single molecule, for example, the available oxygen content of benzene-1,4-dicarboxylate-2,5-diperoxycarboxylic acid (magnesium salt) is approximately 10.8%, whereas for MMPP the available oxygen content is approximately 8.3%, and that this needs to be taken into account in calculating the actual proportion of bleaching agent employed in order to give a specified available oxygen concentration in the washing or bleaching composition or subsequent solution.

OTHER COMPONENTS OF THE WASHING COMPOSITIONS

In addition to MPX, washing compositions according to the present invention contain a surfactant, otherwise elsewhere referred to interchangeably as a surface active agent or tenside or a tensio active agent, which is normally present in an amount in the range of from 5 to 95%, often from 5 to 40%, and in the many embodiments from 8 to 25% by weight of the washing composition. The washing composition also contains one or more builders present in amounts of normally from 1 to 90% by weight, and frequently within the range of from 5 to 70% of the washing composition. The builder is frequently included in a weight ratio to the surfactant of from 1:2 to 10:1. Preferably, sufficient builder is included to provide a washing solution having initially a pH of 7 to 11, in many cases 8.5 to 9.5. If desired, the washing composition can include a filler or processing aid such as sodium sulphate, usually the amount of from 0 to 40% by weight and often at least 5% by weight, at least part of which can be provided in the form of a coating or diluent for the MPX.

SURFACTANTS

The surfactants which can be employed in washing compositions according to the present invention or in conjunction with bleaching compositions according to the present invention can be non-ionic, anionic, cationic, or amphoteric. Generally, the surfactants contain at least one hydrophobic group, e.g. an aliphatic hydrocarbon group containing at least 8 carbon atoms, and often from 10 to 26 carbon atoms, the aliphatic group often being acyclic, but sometimes containing an alicyclic group, or the hydrophobic group can be an alkaryl group containing at least 6 and preferably up to 18 aliphatic carbon atoms. The surfactant contains in addition at least one water-solublising group for example a sulphonate, sulphate, or carboxylic group which is linked either directly or indirectly to the hydrophobic group. Linking members can include residues of polyhydric alcohols containing etheric or esteric linkages, for example derived from ethylene glycol, propylene glycol, glycerine or polyether residues. The surfactants can be soaps or be synthetic, for example as described in chapter 2 of Synthetic Detergents by A. Davidsohn and B. M. Milwidsky, 5th Edition published in 1972 by Leonard Hill, London, and methods of making them are described in chapter 4 of the same book.

Amongst anionic surfactants described on pages 15–23 of the aforementioned book, sulphonates and sulphates are of special practical importance. The sulphonates include, for example, alkaryl sulphonates, and particularly alkyl benzene sulphonates, the alkyl group preferably being straight chain containing 9 to 15 carbon atoms, of which one of the most commonly employed surfactants is linear dodecyl benzene sulphonate. Other anionic sulphonates which are useful in washing compositions containing MPX include olefin sulphonates, obtained, for example, by sulphonating primary or secondary aliphatic mono-olefins, alkene sulphonates, especially linear alkene sulphonates, and hydroxy alkene sulphonates and disulphonates. especially 3-,4-, and 5-,hydroxy-n-alkyl sulphonates in which the alkyl group contains any even number from 10 to 24 carbon atoms. Other desirable anionic surfactants include alcohol sulphates, preferably linear, having a chain length of at least 10 carbon atoms and sulphated fatty acid alkanolamides. Other sulphates comprise sulphated nonionic surfactants as for example alkylphenyl-ethylene oxide ether sulphate in which the alkyl groups contain from about 8 to 12 carbon atoms and there are 1 to 10 units of ethylene oxide in each molecule. Yet other sulphate surfactants comprise alkyl ether sulphates where the alkyl group contains from 10 to 20 carbon atoms, preferably linearly and each molecule contains from 1 to 10 preferably from 1 to 4 molecules or ethylene oxide. Further anionic surfactants include phosphate derivatives of the ethylene oxide based nonionic surfactants described herein.

In practice, cationic detergents are normally not present in the same composition as anionic surfactants, but when cationic detergents are used they are frequently quaternary ammonium salts such as tetraalkyl ammonium halides in which at least one of the alkyl group contains at least 10 carbon atoms or quaternary pyridinium salts substituted by an alkyl chain of at least 10 carbon atoms.

A considerable proportion of nonionic surfactants suitable for use in the present invention comprises condensation products of ethylene oxide and possibly propylene oxide. One class of such nonionic surfactants which is of special importance comprises water soluble condensation products of alcohols containing from 8 to 18 carbon atoms with an ethylene oxide polymer often containing at least 10 molecules of ethylene oxide per molecule of surfactant, e.g. from 10 to 30 moles of ethylene oxide. Particularly desirable nonionic surfactants comprise water soluble condensates of alkyl phenols or alkyl naphthols with an ethylene oxide polymer normally containing from 5 to 25 moles of ethylene oxide per mole of alkyl phenol or alkyl naphthol. The alkyl group normally contains from 6 to 12 carbon atoms and is frequently linear.

As an alternative to the hydrophobic moiety of the nonionic surfactant being linked to the hydrophilic moiety by an ether link as in alkyl phenol ethylene oxide condensates, the linkage can be an ester group. The hydrophobic moiety is normally the residue of a straight chain aliphatic acid containing from 10 to 22 carbon atoms and more particularly lauric, stearic and oleic residues. In one class of nonionic ester surfactants, the hydrophilic moiety comprises polyethylene oxide, frequently in the ratio of from 5 to 30 moles of ethylene oxide per mole of the fatty acid residue. It will be recognised that both mono and di esters can be employed. Alternatively it is possible to employ as the hydrophilic moiety glycerol, thereby producing either mono or di glycerides. In a further group, the hydrophilic moiety comprises sorbitol. A further class of nonionic surfactants comprise alkanolamides in which a C10 to C22 amide is condensed with a polyethylene oxide or polypropylene glycol hydrophilic moiety or moieties. Semipolar detergents include water soluble amine oxides, water soluble phosphine oxides and water soluble sulphur oxides, each containing one alkyl moiety of from 10 to 22 carbon atoms and two short chain moieties selected from the groups of alkyl and hydroxyalkyl groups containing 1 to 3 carbon atoms.

The nonionic and anionic surfactants are often employed together in many cases in a weight ratio within the range 2:1 to 1:10.

Useful amphoteric surfactants include derivatives of aliphatic quaternary ammonium, sulphonium and phosphonium compounds in which the aliphatic moieties can be linear or branched, or two of which can join to form a cyclic compound, provided that at least one of the constituents comprises or contains a hydrophobic group containing from about 8 to 22 carbon atoms and the compound also contains an anionic water solubilising group, often selected from carboxylic, sulphate and sulphonates.

BUILDERS

The builders, sometimes elsewhere alternatively called detergent builders, or builder salts which can be included in the washing compositions of the present invention can be either inorganic or organic. Suitable inorganic builders include pyrophosphates, tripolyphosphates, and higher polymeric phosphates, having the formula $NaP_2O_7(MPO_3)_n$ where M represents an alkali metal cation and n is at least two. Other highly satisfactory inorganic builders include aluminosilicates (faujasites) which can act as cation exchangers for calcium and magnesium cations. Particularly suitable examples of aluminosilicates are zeolite A, characterised in U.S. Pat. No. 2,882,243, zeolite X characterised in U.S. Pat. No. 3,013,990, and mixtures of A and X, preferably in a weight ratio of 50:50 to 15:35 and the zeolites disclosed in U.S. Pat. No. 3,985,669. Other suitable inorganic builders include carbonates and silicates. As is conventional, the inorganic builders are preferably in the form of the sodium salt.

The organic builders which are suitable for inclusion in washing compositions herein include hydroxycarboxylic acids, polycarboxylic acids, aminopoly carboxylic acids and polyphosphonic acids, it being recognised that, as with inorganic builders, the organic builders are normally employed in the form of the sodium salt thereof. It will be recognised that several of the builders could be ascribed to more than one of the classes of builders aforementioned. The polycarboxylic acids can be monomeric such as $C_2$ to $C_{10}$ alpha-omega dicarboxylic acids, or $C_3$ to $C_6$ acyclic compounds substituted by at least three carboxylic acid groups such as 1,1,3,3-propane tetracarboxylic acid or 1,1,3,3,5,5-pentane-hexacarboxylic acid, or aromatic such as benzene pentacarboxylic acid. Alternatively, the polycarboxylic acid can be polymeric for example the polymers of acrylic acid, hydroxyacrylic acid, or maleic acid alone or copolymerised with one another or with olefinically unsaturated compounds such as ethylene, vinyl alcohol, vinyl acetate or acrylamide. Other suitable polycarboxylates include so called "ether polycarboxylates" i.e. ethers in which both aliphatic moieties are short chain and each contains one or more carboxylic acid groups, such as oxydiacetic acid, oxydisuccinic acid or carboxylymethyloxysuccinic acid. Alternatively the ether group forms part of a five membered oxirane group which is substituted by carboxylic acid groups such as furan tetracarboxylic acid or tetrahydrofuran tetracarboxylic acid.

By aminepolycarboxylic acids is meant amines that are substituted by a plurality of carboxylic acid groups, especially acetic acid groups and which may contain a plurality of amine nitrogen atoms linked by dimethylene groups. Such compounds include ethylene diaminetetraacetic acid, diethylene triaminepentaacetic acid, nitrilotriacetic acid and their counterparts in which one of the carboxylic acid groups is replaced by a (2-hydroxyethyl) group.

The polyphosphonic acids are normally alkyl, amino-, or hydroxyalkyl-polyphosphonic acids such as 1-aminoethane-1,1- diphosphonic acid, 1-amino-1-phenyl-1-diphosphonic acid, amino trimethylene-triphosphonic acid, ethylene diamino tetramethylene tetraphosphonic acid, 1-hydroxy ethane-1,1-diphosphonic acid. Related compounds containing one or more carboxylic acid groups can also be employed, such as 1-phosphonoethane-1,2-dicarboxylic acid.

The builder tends to produce a a washing solution in the range pf pH 8.5 to pH 10.5 when the washing compositions are less good.

Naturally, the washing composition can also contain auxiliary agents for washing compositions which are known in themselves such as soil anti-redeposition agents, dye transfer inhibitors, optical brightening agents, stabilisers for peroxyacids, corrosion inhibitors, bactericides, dyes, perfumes, foam enhancers, foam inhibitors, absorbents and abrasives. Such auxillary agents are often present to a total amount of up to 20% by weight of the washing composition, and typically at least 1% and frequently between 1 and 10%.

By way of example, sodium carboxymethylcellulose is of practical importance as a soil antiredeposition agent, and derivatives of diaminostilbene sulphonic acid and 1,3-diaryl-2-pyrazolines, and aminocoumarins are well known optical brighteners. If desired, proteolitic enzymes may also be incorporated as one of the auxillary agents, preferably coated with a nonionic polyethylene glycol surfactant so as to prevent their interaction with the MPX.

If desired, the washing composition can contain in addition to the MPX, one or more inorganic persalts such as sodium perborate monohydrate or tetrahydrate, or sodium percarbonate, for example in a mole ratio to MPX of up to 5:1. Such a combination can be particularly desirable where the washing composition is dissolved in the washing liquor at ambient temperature and the liquor is then heated to a final washing temperature in excess of 60° to 70° C., the rapidly dissolving MPX providing an oxidising bleach at low washing temperatures and the persalt remaining to continue the bleaching at the high washing temperatures.

It will be recognised that MPX generates in aqueous solution a peroxyacid anion. In consequence, if desired, the washing compositions of the present invention can incorporate an aldehyde or ketone peroxyacid activator as described in U.S. Pat. No. 4,005,029, e.g. 8-hydroxy quinoline which is a well-known peroxygen stabiliser.

An alternative to incorporating MPX and the other components in washing compositions, it is contemplated within the scope of the instant invention for the user to employ a base washing composition, i.e. a composition free from MPX but having components as described hereinbefore and employ in conjunction therewith a bleaching composition containing MPX, for example as a granulate, or in a tablet, or in a water soluble or water dispersible sachet or in a porous container through which the MPX can leach out into the wash liquor. Moreover it will be a recognised that the MPX in granulate, tablet or similar form need not be added during the washing stage, but by virtue of its high rate of solubility, even at ambient temperature, it can also be employed in subsequent stages, for example the rinsing stage. When tablets of the MPX are formed, for example by compaction of granules of desensitised MPX, it is preferable to incorporate within them one or more disintegrating aids, conventionally micro-fine starch or micro crystalline cellulose, normally in an amount of up to 2% w/w on the tablet.

The bleaching composition can comprise any composition containing MPX and any diluents described herein, but in practise, the MPX content is usually within the range 40 to 60% and the other components so selected as to be readily water soluble or dispersible at ambient temperature. Especially suitable bleaching compositions comprise (i) 100 parts by weight of particulate MPX as produced by the processes described hereinbefore (i.e. a particulate product often containing at least 30% MPX, calculated as the anhydrous compound, and preferably from 60 to 70% MPX), (ii) from 10 to 50 parts by weight in total of one or more of (a) the salts of halogen-free acids, (b) inorganic builders and (c) un-reactive organic builders, such as amine polycarboxylates and phosphonates and (iii) any disintegrating acid, bleach activator or stabiliser in amounts in total of up to 10 parts by weight. When the bleaching composition is intended for use without any other washing composition being employed in direct conjunction with it, one occasion being in the rinsing stage of clothes washing, sufficient builder preferably is present to produce a pH in the range of 7.5 to 9.

It is highly desirable for MPX bleaching compositions to be granulated agglomerated or otherwise aggregated to produce particles within the range of 0.01 mm to 2 mm, particularly from 0.05 mm to 1 mm and especially from 0.2 mm to 1.0 mm so as to match the particle size ranges of the other components in washing formulations and thereby minimise problems of segregation which could arise during transportation and handling of the product.

Washing processes according to the present invention can be carried out at a temperature from ambient up to the boiling point of the washing solution. Compositions according to the present invention are particularly well suited to a process at which washing or bleaching is carried out by steeping at ambient or by heating the solution to a temperature from about 25° to 60° C. Alternatively the washing and bleaching processes may be effected by heating up a cold washing solution. A combination of processes can be used, such as cold steeping followed by a wash at 30°, 40° or 50° C.

In general, it is desirable for washing or bleaching solutions for use in the home to contain at least 1 part per million available oxygen (Avox.) preferably at least 5 part per million Avox. Household washing solutions prepared by dissolution of detergent compositions in general provide no more than about 200 ppm. Avox., frequently no more than 100 ppm Avox. and in many cases in the range of 25 to 100 ppm Avox.

In general, the rate of removal of stains is enhanced by employing a higher temperature and by higher Avox. concentrations. By virtue of the rapid rate at which MPX dissolves in water or aqueous detergent solutions, the contact period between solution and fabric can conveniently be as short as 5 minutes. Longer periods of for example, up to 1 hour tend to provide greater soil removal. In cold washing or steeping even longer periods can be employed, such as steeping overnight.

Many washing compositions are formulated so as to extract stains from fabrics into solution and to minimise the redeposition of such stains or dye transfer onto the fabric. Consequently, it is extremely desirable for the bleaching agent to be able to bleach stains in solution, and in this respect MPX is particularly useful on account of its comparatively high rate of solubility in aqueous alkaline solutions, thereby enabling the peroxyacidic species to be present in solution when the stains are extracted. However, even though MPX provides a more active bleaching species, damage to the dyestuffs in coloured fabrics is comparable with that caused by inorganic peroxygen compounds employed heretofore, and thus enables washing compositions containing MPX to be employed for coloured fabrics as well as for whites. Indeed, it would appear that, advantageously, as measured by standard tests, MPX causes only similar dye damage to that caused by MPPA from which it is derived i.e. an acceptable level, but less than that caused by the analogous sodium salt.

In addition to washing and/or bleaching fabrics, the compositions can be used to clean hard surfaces such as metal, plastic or wooden surfaces, either by dissolving washing or bleaching compositions in water, preferably to provide 200 ppm to 500 ppm avox or by forming a slurry or paste of such compositions. Also, if desired, solutions produced by the dissolution of compositions described herein can be used to bleach textile fabrics, wood or pulp under the conditions, and employing the equipment used for bleaching such articles with hydrogen peroxide or inorganic peroxoacids.

Having described the invention in general terms, specific embodiments will be described more fully by way of example. Modifications to the following can be made by the skilled artisan without departing from the spirit of the invention.

EXAMPLES

EXAMPLE 1

In this Example MMPP was prepared by dissolving water (50 ml) and then hydrogen peroxide (87.5% w/w, 50 ml) in ethyl acetate (1000 ml). The temperature of the solution was then reduced to 10° C. and so maintained during the introduction of particulate phthalic anhydride (250 g) and magnesium oxide (33.8 g) with vigorous stirring, forming a slurry. The temperature of the slurry was allowed to rise thereafter to 20°-25° C. and the mixture continued to be stirred for a further three hours, during which time crystalline hydrated MMPP precipitated out. The crystals were then filtered off, washed with a small volume of ethyl acetate and dried under vacuum. The yield was 270 g and analysis showed an available oxygen (Avox) content of 5.44% by weight, and that the product contained peroxyacid and was free from diphthaloyl peroxide. A similar product and yield occured when the slurry was stirred for only one hour after its formation instead of 3 hours.

EXAMPLE 2

Example 1 was followed except that 100 ml of aqueous hydrogen peroxide (50% w/w) was employed in the process instead of 50 ml water and 50 ml of 87.5% solution, and the magnesium oxide was introduced progressively over about 30 minutes. The resultant product on analysis was substantially the same as that of Example 1.

EXAMPLE 3

Example 2 was followed except that magnesium hydroxide (50 g) was employed instead of magnesium oxide. The yield and product analysis was substantially the same as in Example 2.

EXAMPLE 4

Example 2 was followed except that it was effected on a tenth scale and that basic magnesium carbonate ($3MgCO_3.Mg(OH)_2.3H_2O$, 7.69 g) was employed instead of magnesium oxide. The yield was one tenth the yield of Example 2 and product analysis was substantially the same as in Example 2.

EXAMPLE 5

In this Example MMPP was prepared by dissolving phthalic anhydride (25 g) and magnesium oxide (3.4 g) in ethyl acetate (100 ml), and the solution cooled to 10° C. and maintained at that temperature with stirring during the introduction of aqueous hydrogen peroxide (10 ml, 50% w/w) over a period of 10 minutes. The temperature of the slurry was allowed to rise to ambient temperature and the slurry continued to be stirred for one hour. The precipitated hydrated MMPP was filtered off, washed with ethyl acetate and dried out under vacuum. The yield was 26 g, the product having an Avox of 5.3% by weight.

EXAMPLE 6

Example 2 was followed except that the temperature was allowed to rise to 20° C. during the introduction of the phthalic anhydride. Although the yield by weight and Avox content of the product was substantially as in Example 2, it contained approximately 5% w/w diphthaloyl peroxide (from IR spectroscopy).

EXAMPLE 7

In this Example, the process of Example 1 was followed except that it was effected in a tenth scale and 10 ml water used instead of 5 ml. The yield of product was 30.5 g but its Avox was only 3.07%.

EXAMPLE 8

In this Example, Example 2 was followed except that it was effected on a tenth scale and 70% w/w hydrogen peroxide (65 ml) was employed instead of 50% w/w hydrogen peroxide. The yield was 4.2 g, the product having an Avox of 2.64% from MMPP and 0.24% from $MgO_2$. The filtrate was left overnight and a further 17.6 g solid precipitated out, having an Avox of 2.29% and an MMPP content of 27.7%.

EXAMPLE 9

In this Example, Example 8 was followed, except that 87.5% hydrogen peroxide solution (50 ml) was employed instead of 70% solution. The initial yield was only 1.9 g, the product containing 18.5% w/w MMPP contributing 1.53% Avox and 1% $MgO_2$. The filtrate when left overnight yielded a further 19 g of a product containing 34.6% MMPP. From this Example and Examples 7 and 8 can be seen the benefit of employing approximately 50% hydrogen peroxide solution.

EXAMPLE 10/COMPARISON 10

The rate of production of diphthaloyl peroxide during storage of MMPP was compared with that for MPPA under identical conditions, in vessels open to the atmosphere at 30° C. or 80° C.

The results are summarised in Table 1.

TABLE 1

| | Compound | Temperature | Time | % DPP formed |
|---|---|---|---|---|
| C 10a | MPPA | 80° C. | 69 hours | 30 |
| Ex 10a | MMPP | 80° C. | 69 hours | 0 |
| C 10b | MPPA | 30° C. | 127 days | 20 |
| Ex 10b | MMPP | 30° C. | 127 days | 0 |

From Table 1 it can be seen that MMPP did not form detectable amounts of diphthaloyl peroxide, whereas MPPA did.

EXAMPLE 11/COMPARISONS 11A-D

In this Example/Comparison, the stability of MMPP as compared with MPPA and the corresponding sodium monoperoxyphthalate (SMPP) potassium monoperoxyphthalate (KMPP) and ammonium monoperoxyphthalate (NMPP) by themselves on storage at 30° C. in containers open to the atmosphere.

The Avox content of the samples was measured before and after the storage period of 28 days and the loss of Avox calculated as a % of the original. The results are summarised in Table 2 below.

TABLE 2

| | Compound | Avox loss as % |
|---|---|---|
| C 11a | MPPA | 15 |
| C 11b | SMPP | 26 to 87 |
| C 11c | KMPP | 71 |
| C 11d | NMPP | 97 (after 1 week) |
| Ex 11 | MMPP | 0 to 8 |

From Table 2 it can be seen that MMPP was markedly the most stable under the test conditions.

The detergent base compositions used in subsequent Examples were approximately as given in Table 3, %'s being by weight.

TABLE 3

| | % in composition | | |
|---|---|---|---|
| Component | A | B | C |
| Sodium tripolyphosphate | 32 | | 44 |
| Sodium silicate | 15 | | 14 |
| Sodium carbonate | 1 | 12 | |
| Sodium silicate/zeolite A mix | | 27 | |
| Sodium sulphate | 22 | 36 | |
| Sodium salt of linear alkyl Benzene sulphonate | 14 | 15 | 7 |
| Soap | | | 6 |
| Nonionics | 3 | 5 | 5 |
| Detergent adjucts (including CMC, EDTA, OBA) | 1 | 1 | 1 |
| Water | | balance | |

EXAMPLE 12/COMPARISON 12

In this Example and comparison, MMPP was compared with SMPP. Samples of the salts were thoroughly mixed to provide initial avox content of 0.035 g, with 4 g of Base Detergent Composition C.

The mixture was then sealed in a glass tube and stored at 28° C. for 4 weeks. The avox content was then determined again and the avox loss calculated by difference.

The results are shown as a % of the original avox content in Table 4.

TABLE 4

| | Compound | Avox loss as % |
|---|---|---|
| C 12 | SMPP | 31 |
| EX 12 | MMPP | 1 |

From Table 4 it can be seen that the most stable alkali metal salt in the test described in Example 10 was markedly less stable than MMPP under the conditions of this test.

EXAMPLE 13/COMPARISON 13A-B

In this Example/comparison the dye damage of standard PROCION red and blue cotton fabrics was tested by washing the fabrics with solutions containing 4 gpl of Base Detergent Composition A, and sufficient bleaching agent to provide 20 ppm Avox. Each fabric was washed 5 times at 40° C. for 10 minutes with fresh samples of the aforementioned solution at pH 9. Fading of the fabrics was calculated and expressed as ΔE, and the results are summarised in Table 5.

TABLE 5

| | | ΔE | |
|---|---|---|---|
| | Product | Red | Blue |
| C 13a | SMPP | 2.6 | 3.3 |
| C 13b | MPPA | 2.0 | 1.9 |
| Ex 13 | MMPP | 1.9 | 1.8 |

From Table 5, it can be seen that under the test conditions, the fading caused by MMPP was less than that caused by the sodium salt and very slightly less than for MPPA.

EXAMPLES 14 TO 36

In Examples 14 to 36, the effectiveness of MMPP at removing soil from household fabrics was measured by washing swatches of cloth, normally cotton, unless otherwise specified, which had been pre-stained under a range of conditions including temperature and concentrations. The trials were made by either mixing together a detergent base with the appropriate amounts of MMPP composition and then dissolving the mixture in water or dissolving both components separately in the water, the water having been heated to the decided temperature and maintained until that temperature for the given period.

The trials were carried out in a laboratory scale washing machine sold under the name "Tergotometer by the U.S. Testing Corporation which simulates the action of a vertical agitator type of domestic washing machine. In each trial, concentration of detergent base composition employed was 4 gpl in the washing solution except for Examples 20 to 25 and the corresponding comparison where only 2 gpl Detergent Base concentration was used. In each trial, the water used had a hardness of 250 ppm in a weight ratio of Ca:Mg of 3:1.

After being washed, each swatch was rinsed with cold water and dried. The reflectance of the swatch was then determined and compared with its original reflectance to give a measure of stain removal, using a Zeiss ELREPHO Reflectance Photometer using a Xenon lamp light source equipped with a y-tristimulus filter. Each swatch was measured four times with a backing of three thicknesses of material. The reflectance readings were averaged and the percentage stain removal was obtained from the following formula:

% Stain Removal = $100 \times (R_f - R_i)/R_u - R_i)$ where $R_u$ means reflectance of the unstained cloth $R_i$ means reflectance of the cloth after staining, and $R_f$ means reflectance of the stained cloth after bleaching.

The alkalinity of the washing solutions was measured initially ($pH_i$) and at the end ($pH_f$).

EXAMPLES 14 TO 19

In these Examples, the stain employed was red wine on cotton obtained from EMPA, St. Gallent, Switzerland. The washing solution was buffered to pH 9 with sodium carbonate, but in the comparison, the solution was allowed to retain the natural pH of the base compositions (9.4).

The washing temperature was 40° C. for the washing periods specified in Table 6.

The results are summarized in Table 6.

TABLE 6

| | Product added gpl | Equivalent Avox (ppm) | % Soil Removal | |
|---|---|---|---|---|
| | | | 10 mins | 20 mins |
| C 14 | — | — | 40.1 | 43.6 |
| Ex 14 | 0.3 | 15 | 50.6 | 53.2 |
| Ex 15 | 0.5 | 25 | 53.9 | 60.6 |
| Ex 16 | 0.5 | 35 | 57.6 | 64.9 |
| Ex 17 | 0.95 | 50 | 61.4 | 74.7 |
| Ex 18 | 1.45 | 75 | 65.9 | 82.0 |
| Ex 19 | 1.9 | 100 | 75.5 | 89.9 |

From this Table it can be seen that the soil removal increases progressively as the amount of MMPP present in solution increases, as also as the washing time is increased from 10 to 20 minutes at 40° C. (104° F.).

EXAMPLES 20 TO 25

In these Examples the stain employed was also the EMPA red wine stain, and the detergent base was Base B at 2 gpl concentration in the washing solution. The trials were affected at 40° C. for 10 or 20 minutes as specified in the Table. The pH of the solution was permitted to find its natural level. Separate bleach compositions were made and introduced into the washing solution at 1.6 gpl concentration together with the detergent base, and the amount of components employed was sufficient to provide 35 ppm Avox in solution. The MMPP used was the product of Example 2. The results of the trials are summarised in Table 7 below.

TABLE 7

| | Dry Bleach | | | Avox | % Stain Removal | | pH | |
|---|---|---|---|---|---|---|---|---|
| | MMPP | Na$_2$CO$_3$ | Na$_2$SO$_4$ | (ppm) | 10 mins | 20 mins | pH$_i$ | pH$_f$ |
| C 20 | — | — | — | — | 36.0 | 39.2 | 9.4 | 9.1 |
| Ex 20 | 0.65 | 0.1 | 0.85 | 35 | 69.8 | 73.1 | 8.5 | 8.1 |
| Ex 21 | 0.65 | 0.4 | 0.55 | 35 | 50.1 | 59.4 | 9.1 | 8.5 |
| Ex 22 | 0.65 | 0.8 | 0.15 | 35 | 43.4 | 50.0 | 10.0 | 9.2 |
| Ex 23 | 1.10 | 0.1 | 0.4 | 60 | 70.2 | 80.9 | 8.1 | 7.8 |
| Ex 24 | 1.10 | 0.2 | 0.3 | 60 | 73.6 | 80.5 | 8.5 | 8.1 |
| Ex 25 | 1.10 | 0.4 | 0.1 | 60 | 68.2 | 78.3 | 9.0 | 8.8 |

Table 7 demonstrates that excellent soil removal can be obtained especially when the initial and final pHs of the washing solutions are in the range of pH 7.5 to pH 9.

EXAMPLES 26 TO 28

In Examples 27 and 28 MMPP produced by the method of Example 2 (100 parts by weight) was granulated with 20 parts by weight of either magnesium sulphate or sodium sulphate. The granulate was mixed with detergent base A, in a ratio to give a 4 gpl base A concentration and 35 ppm avox concentration (i.e. 0.78 g granulate per 4 g base A). In Example 26 granulated MMPP was employed. The washing was carried out at 40° C. and at the natural pH of the solution. The stain was a further EMPA red wine stain.

The results are summarised in Table 8 below.

TABLE 8

| | % Stain Removal | | pH | |
|---|---|---|---|---|
| Bleach | 10 mins | 20 mins | pH$_i$ | pH$_f$ |
| Ex 26 | 55.9 | 69.4 | 8.8 | 8.7 |
| Ex 27 | 67.0 | 78.8 | 8.7 | 8.1 |
| Ex 28 | 63.6 | 76.1 | 8.6 | 8.3 |

From Table 8 it can be seen that granulated MMPP with either magnesium sulphate or sodium sulphate improved the washing performance.

EXAMPLES 29 TO 36

In these Examples, MMPP was employed at 35 ppm Avox in solution together with detergent base A to remove stains from the cloths and under the conditions specified in Table 7. The solution was allowed to adjust its natural pH. The results are summarised in Table 9.

TABLE 9

| | Stain | Temp °C. | % Soil Removal | | pH | |
|---|---|---|---|---|---|---|
| | | | 10 mins | 20 mins | pH$_i$ | pH$_f$ |
| Ex 29 | EMPA red wine | 70 | 79.2 | 93.6 | 8.7 | 8.4 |
| Ex 30 | Coffee | 70 | 66.9 | 70.7 | 8.7 | 8.3 |
| Ex 31 | EMPA red wine | 25 | 49.7 | 58.0 | 8.8 | 8.7 |
| Ex 32 | EMPA red wine | 40 | 56.1 | 70.0 | 8.7 | 8.6 |
| Ex 33 | Tea | 25 | 10.9 | 18.0 | 8.9 | 8.7 |
| Ex 34 | " | 40 | 35.9 | 45.4 | 8.7 | 8.7 |
| Ex 35 | Coffee | 25 | 37.4 | 45.5 | 8.9 | 8.8 |
| Ex 36 | " | 40 | 51.2 | 57.4 | 8.7 | 8.5 |

From Table 9 it can be seen that MMPP can be employed effectively at 25° C. up to 70° C.

EXAMPLES 38–41

In these Examples, particulate washing compositions were prepared by admixing a preformed particulate bleaching composition with spray dried Detergent Base C, in the weight ratios specified in Table 10. In all four Examples the particles of MMPP employed had been prepared by the process according to Example 2 containing 65% w/w MMPP calculated as the anhydrous salt. The bleaching composition in Example 38 was made by dry mixing particles of MMPP with sodium tripolyphosphate, (STPP) spraying with a small quantity of water, drying and sieving the agglomerate to retain a particle size range of 0.25 to 0.50 mm.

In Examples 39, 40 and 41, the bleaching composition was obtained by spraying on to MMPP particles an ethereal solution of the agent in a rotating pan and evaporating off the solvent.

TABLE 10

| | Bleaching Composition Components/parts by weight | Detergent Base C parts by weight |
|---|---|---|
| Ex 38 | MMPP/260 STPP/52 | 1600 |
| Ex 39 | MMPP/260 Myristyl alcohol/52 | 1600 |
| Ex 40 | MMPP/260 Lauric acid/52 | 1600 |
| Ex 41 | MMPP/260 di-n-butyl phthalate/13 | 1600 |

EXAMPLE 42

In this Example, the filtrate separated from the MMPP product was recycled. In the first cycle, ethyl acetate (900 g), aqueous hydrogen peroxide (86.5% by weight $H_2O_2$, 33 g) and demineralised water (24.3 g) were mixed to form an homogenous phase, and the mixture cooled to about 10° to 12° C. Particulate phthalic anhydride (125 g) and magnesium oxide (86% by weight as Mg O, 16.84 g) were than introduced with stirring, the temperature being maintained at about 10°-12° C. by cooling throughout the addition and for 15 minutes thereafter. The temperature of the mixture was allowed to rise to 18° to 20° C. and was maintained in that range for a further hour, the mixture being stirred throughout. The mixture was then cooled to 10° C. and filtered under vacuum. The solid product MMPP was washed with further ethyl acetate (50 g) dried and the yield was 128 g, having an avox of 5.8% by weight.

For the second and subsequent cycles the filtrate and ethyl acetate washing liquor were combined and a small further amount of ethyl acetate added to restore the volume of the final mixture to its original level. This further amount ranged within 18 g to 10 g. The second and subsequent cycles followed the same series of steps as the first cycle but lower amounts of reagents were employed, namely 19 g of 86.5% aqueous hydrogen peroxide, 16 g of demineralised water, 63.84 g of phthalic anhydride and 16.84 g magnesium oxide. These amounts represented approximately the amounts which it had been determined from the level of residual in the recycled filtrate/washing were needed to restore the levels of the reagents to a steady state on third and subsequent cycles. The yield of solid product in the second to fifth cycles averaged 110 g and ranged from 108 to 113 g, at an Avox content of 5.6% on average and ranging from 5.43 to 5.76% by weight. It was observed that by the fifth cycle a significant proportion of the product was in granular form.

EXAMPLE 43

In this Example water (5 ml) and then hydrogen peroxide (87.5% w/w, 0.169 mole) was dissolved in ethyl acetate (100 ml), and the temperature of the solution was then reduced to approximately 5° C. and so maintained during the introduction of particulate pyromellitic anhydride (0.0845 mole) followed immediately by magnesium oxide (0.0845 mole) with vigorous stirring, forming a slurry. The temperature of the slurry was allowed to rise after about 5 minutes to 20-25° C. and the mixture continued to be stirred for a further hour, during which time a crystalline hydrated salt precipitated out. The crystals were then filtered off, washed wth a small volume of ethyl acetate and dried under vacuum. The yield was 22.4 g and analysis showed an available oxygen (Avox) content of 4.59% by weight and a product free from diacyl peroxide.

EXAMPLE 44

In this Example, the process described in Example 43 was followed, except that trimellitic anhydride (0.169 mole) was employed instead of pyromellitic anhydride. A solid agglomerate was obtained as the reaction product in an amount of 28.9 g, having an Avox of 2.07% by weight. A small residual amount of magnesium oxide was present in the product. Examination of the infra-red spectrum of the product indicated that there was strong absorption assignable to a carboxylic acid group in addition to strong absorption assignable to a carboxylate ion group.

EXAMPLE 45

The process of Example 44 was repeated, except that the amount of trimellitic anhydride used was reduced to 0.050 moles, the amount of hydrogen peroxide (87% w/w) reduced to 0.05 mole, the amount of magnesium oxide reduced to 0.032 mole, the amount of water reduced to 3.6 ml and ethyl acetate reduced to 40 ml. The reaction conditions were as in Examples 1 and 2. The product had an Avox of 1.87% and appeared to be free from magnesium oxide.

EXAMPLE 46

In this Example, maleic anhydride (0.0170 moles) was mixed with ethyl acetate (50 ml) and the mixture cooled to approximately 5° C. Magnesium oxide (0.085 moles) was then introduced, followed by a solution of hydrogen peroxide (87% w/w, 0.18 moles) and demineralised water (5 ml) in ethyl acetate (50 ml), with constant stirring. After stirring for a further hour, during which time the temperature of the mixture was permitted to rise but still maintained at below 23° C., the resultant solid was filtered off, washed with a further portion of ethyl acetate and dried under vacuum. The yield was 21.5 g having an Avox content of 5.05%. The infra-red spectrum of the product demonstrated that it appeared to be substantially free from carboxylic acid groups and diacyl peroxide, and there was no evidence of epoxidation of the olefinic double bond.

EXAMPLE 47

In this Example, the process employed in Example 46 was followed except that 0.17 mole of citraconic anhydride was employed instead of maleic anhydride. The resultant product was obtained in a yield of 23.5 grams having an avox content of 5.62%. Once again, the infrared spectrum demonstrated the presence of peroxycarboxylic acid and carboxylate groups, and the product appeared to be substantially free from carboxylic acid groups, diacyl peroxides and epoxide groups.

EXAMPLE 48

In this Example, a further variation in the method of introducing the reactants was employed. Maleic anhydride (0.51 mole) was dissolved in ethyl acetate (300 ml) and the mixture cooled by contact with an ice bath to a temperature not above 5° C. Particulate magnesium oxide (0.255 mole) was then stirred into the mixture. A solution of hydrogen peroxide (87.3%, 0.514 moles) diluted with 15 ml of demineralised water was then introduced into the reaction mixture progressively over a period of 40 minutes with constant stirring, the reaction mixture remaining in contact with the ice bath so that its temperature never rose above 20° C. and often was about 5° C. After removal of the ice bath, the mixture was stirred for a further one hour and ten minutes, the temperature remaining below 20° C. throughout. The resultant product was filtered off, and washed with ethyl acetate and dried under vacuum. The yield of product was 71.2 grams having an avox content of approximately 5.4% by weight.

The infra-red spectrum indicated that the active oxygen-containing compound was the salt of monoperoxy maleate.

EXAMPLE 49

In this Example, cyclohexane-1,2-dicarboxylic anhydride (0.085 mole) was dissolved in ethyl acetate (50 ml) and solid magnesium oxide (0.042 mole) was introduced into the mixture. As in example 6, the reaction mixture was maintained in contact with an ice bath throughout the introduction of the reactants. Aqueous hydrogen peroxide (87.6% w/w, 0.086 mole) was diluted with demineralised water (2.5 ml) and then introduced over a period of 5 minutes into the reaction mixture, with stirring. Thereafter, the mixture was stirred for a further hour, its temperature being permitted to rise but maintained throughout at below 23° C. A small portion of ethyl acetate was then added to the reaction mixture and the product filtered off, washed with a further small portion of ethyl acetate and dried under vacuum. The yield of product was 7.74 g having an available oxygen content of approximately 4.3% by weight, and infra-red spectrocscapy indicated that the active oxygen containing compound was magnesium monoperoxy hexahydrophthalate, otherwise referred to as a magnesium salt of cyclohexane-1-carboxylate-2-peroxycarboxylic acid. From the infra-red spectrum of the product, it was apparent that some carboxylic acid groups were present.

EXAMPLES 50 TO 59

In Examples 50 to 59, the effectiveness of the products obtained in Examples 43, 45, 47, 48 and 49 at removing soil from household fabrics was measured by washing swatches of cotton cloth, which had been prestained with red wine and obtained from EMPA, St Gallent, Switzerland at 40° C. The trails were made by either mixing together a detergent base with the appropriate amounts of magnesium persalt and then dissolving the mixture in water or dissolving both components separately in the water, the water having been heated to the decided temperature and maintained at that temperature for the given period, in the same way and using the same apparatus as Examples 14 to 36.

In Examples 50 to 54 the solution was permitted to change pH during washing and the alkalinity of the washing solutions was measured initially (pH$_i$) and at the end (pH$_f$), whereas in Examples 55 to 57 and 59, the washing solution was buffered to pH 9 with sodium bicarbonate, and Example 58 with sodium carbonate.

The results are summarised in Tables 11 and 12 respectively.

TABLE 11

| Ex No | Bleaching Agent produced in Ex No | Solution pH | | % stain removal after | |
|---|---|---|---|---|---|
| | | pH$_i$ | pH$_f$ | 10 min | 20 min |
| 50 | 45 | 9.0 | 8.9 | 32 | 36 |
| 51 | 43 | 9.5 | 9.2 | 48 | 52 |
| 52 | 47 | 9.1 | 8.9 | 50 | 58 |
| 53 | 48 | 8.7 | 8.6 | 53 | 60 |
| 54 | 49 | 9.5 | 9.3 | — | 54 |

TABLE 12

| Ex No | Bleaching Agent produced in Ex No | % stain removal after | |
|---|---|---|---|
| | | 10 min | 20 min |
| 55 | 45 | 33 | 39 |
| 56 | 43 | 43 | 52 |
| 57 | 47 | 47 | 54 |
| 58 | 48 | 51 | 58 |
| 59 | 49 | 53 | 61 |

I claim:

1. In solid form, the magnesium salt of:

Class (1) an aromatic carbocyclic compound substituted around the aromatic nucleus by a carboxylate group and a peroxycarboxylic acid group both groups being derivable from the corresponding aromatic carbocyclic anhydride by reaction with hydrogen peroxide, said aromatic carboxylic compound optionally being further substituted by at least one of the groups selected from alkyl, carboxylate, sulphonate, nitro, chloro and bromo groups or Class (2) a cycloaliphatic compound substituted around the cycloaliphatic nucleus by a carboxylate group and a peroxycarboxylic acid group both groups being derivable from the corresponding cycloaliphatic carbocyclic anhydride by reaction with hydrogen peroxide, said cycloaliphatic carboxylic compound optionally being further substituted by at least one of the groups selected from alkyl, carboxylate, sulphonate, nitro, chloro and bromo groups or Class (3) compounds other than those in class 1 in which the carbonyl group of the peroxycarboxylic acid substitutent is conjugated with the carbonyl group of a carboxylate substituent via olefinic unsaturation which carboxylate and peroxycarboxylic acid substituents are derivable from the coresponding anhydride by reaction with hydrogen peroxide.

2. A salt according to claim 1 characterised in that the aromatic nucleus in Class 1 is a benzene nucleus and the cycloaliphatic nucleus in class (2) is a cyclohexane nucleus.

3. A salt according to claim 2 characterised in that it has the formula

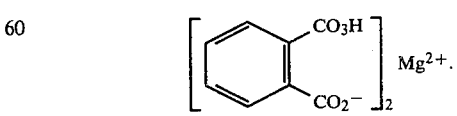

4. A salt according to claim 3 in hydrated form.

5. A salt according to claim 1 selected from the group consisting of magnesium monoperoxymaleate, magnesium monoperoxycitraconate and magnesium salt of cyclohexane 1-carboxylate-2-monoperoxycarboxylic acid.

6. A process for the production of magnesium salts comprising the steps of (1) forming a reaction mixture consisting essentially of
   (a) an organic acid containing a carboxylic acid group and peroxycarboxylic acid group or anion of said organic acid according to class 1, 2 or 3 described in claim 1 herein;
   (b) a magnesium compound which is a base relative to the carboxylic acid group of said organic acid; and
   (c) a solvent from which the resultant salt produced in the process precipitates,
      (ii) maintaining the reaction mixture at a temperature of not more than 30° C. until at least some magnesium salt of the organic acid has precipitated therefrom and
      (iii) separating the precipitated magnesium salt from the spent reaction mixture.

7. A process according to claim 6 characterised in that the solvent is a low molecular weight aliphatic ester.

8. A process according to claim 6 wherein the compound in class 1, 2 or 3 is obtained by reaction between hydrogen peroxide and the corresponding anhydride, in the course of which reaction the anhydride linkage is oxidatively cleaved to generate the peroxyacid group and the carboxylate group and the other substituents of the anhydride, if any, remain in the same relative positions.

9. A process according to claim 8 wherein hydrogen peroxide and the anhydride are reacted in a mole ratio of from 1:1 to 2:1.

10. A process according to claim 9 the wherein hydrogen peroxide and the anhydride are reacted in a mole ratio of from 1.01:1 to 1.2:1.

11. A process according to claims 8 or 10 wherein the hydrogen peroxide is employed as an aqueous solution having a concentration of 40 to 60% by weight hydrogen peroxide based upon the total amount of hydrogen peroxide and water introduced.

12. A process according to claims 8 9 or 10 wherein the amount of aqueous hydrogen peroxide solution employed is less than the amount at which it forms an emulsion with the solvent.

13. A process according to claim 8 characterised in that the reaction temperature is maintained at not more than 15° C. during the period when the anhydride and hydrogen peroxide are brought into contact, and for up to 15 minutes thereafter.

14. A process according to claim 6 characterised in that the magnesium compound employed is magnesium oxide, hydroxide, carbonate or a basic carbonate.

15. A process according to claim 8 wherein the anhydride is phthalic anhydride.

16. A process according to claims 6, 8 or 15 characterised in that the mole ratio of the magnesium compound to the organic acid/anion introduced as such or generated in situ from the corresponding anhydride is from 1:2 to 1.2:2 in which to represent the number of carboxylate groups in the organic acid/anion are formed from the anhydride.

17. A process according to claim 6 characterised in that the reaction between the magnesium compound and the organic acid/anion is carried out at from 15° to 30° C.

18. A process according to claim 17 characterised in that reaction period at 15° to 30° C. is from 0.5 to 5 hours.

19. A process according to claims 8, 12 or 14 characterised in that the aqueous hydrogen peroxide and solvent are mixed to form an homogeneous phase into which is introduced the anhydride and magnesium compound, sequentially or simultaneously.

20. A process according to claim 8 characterised by separating the solid magnesium salt from the liquid phase, at the end of the reaction period, determining as necessary the residual contents of anhydride, monoperoxy acid, hydrogen peroxide and magnesium compound in the liquid phase and recycling the liquid phase for reaction in a subsequent cycle after make-up of the reagents, taking into account the aforementioned residual contents.

21. A process according to claim 20 characterised in that the reagents are introduced during make-up in the mole ratio of magnesium compound to anhydride of from 5:4 to 4:5 and hydrogen peroxide to anhydride of from 1.1:1 to 1.3:1, the anhydride being added in an amount of from 0.35 to 0.75 moles per 1000 g reaction mixture.

22. A process according to claims 20 or 21 characterised in that the anhydride is phthalic anhydride.

* * * * *